United States Patent [19]
Nomura et al.

[11] Patent Number: 5,976,463
[45] Date of Patent: Nov. 2, 1999

[54] PUMP-OXYGENATOR

[75] Inventors: Chifuru Nomura, Nagano-ken; Manabu Hioura, Aichi-ken, both of Japan

[73] Assignees: Shigehisa Amano, Aichi-ken; SN Seiki Co., Ltd., Nagano-ken, both of Japan

[21] Appl. No.: 08/788,644

[22] Filed: Jan. 27, 1997

[30] Foreign Application Priority Data

| Jan. 25, 1996 | [JP] | Japan | 8-011229 |
| Sep. 3, 1996 | [JP] | Japan | 8-233468 |
| Jan. 20, 1997 | [JP] | Japan | 9-007755 |

[51] Int. Cl.$^6$ .............. A61M 1/14; A61M 1/34; A61M 1/36
[52] U.S. Cl. .................................. 422/45; 604/4
[58] Field of Search ............... 422/44–48; 604/4–6

[56] References Cited

U.S. PATENT DOCUMENTS

| 2,792,002 | 5/1957 | Malmros et al. | 422/45 |
| 2,896,620 | 7/1959 | Tremblay | 422/45 |
| 3,175,555 | 3/1965 | Ling | 422/45 |
| 3,191,600 | 6/1965 | Everett . | |
| 3,468,631 | 9/1969 | Raible et al. | 422/45 |
| 3,890,969 | 6/1975 | Fischel | 128/214 |
| 4,466,804 | 8/1984 | Hino | 604/4 |
| 4,490,331 | 12/1984 | Steg, Jr. . | |
| 4,968,483 | 11/1990 | Muller et al. | 422/45 |
| 5,152,964 | 10/1992 | Leonard | 422/48 |
| 5,270,005 | 12/1993 | Raible . | |
| 5,382,407 | 1/1995 | Leonard | 422/48 |
| 5,514,335 | 5/1996 | Leonard et al. | 422/46 |

OTHER PUBLICATIONS

Koyama et al. "Usefulness of 'Low–Vacuum Suction Method' for Cardiopulmonary Bypass" Artificial Organs vol. 24, No. 2 (1995), pp. 595–599.

Hioura et al. "Trial of a Roller Pump–less Heat–lung System" published by American Society of Extra–Corporeal Technology; conference held Mar. 1996.

Official Conference Program of the American Society of Extra–Corporeal Technology International Conference held Mar. 8–11, 1996, Dallas Texas (3 pages).

*Primary Examiner*—John G. Weiss
*Assistant Examiner*—Ki Yong O
*Attorney, Agent, or Firm*—Birch, Stewart, Kolasch & Birch, LLP

[57] ABSTRACT

In a pump-oxygenator, artificial lungs are located in a blood delivery line for adding oxygen to a blood stream flowing through the blood delivery line and removing carbonic acid gas therefrom. A plurality of sub-reservoirs are located upstream of a main reservoir to store blood therein. A plurality of sub-suction lines for blood are respectively connected to the plurality of sub-reservoirs. The pump is driven to supply a negative pressure with the main reservoir, a magnitude of which is smaller than a negative pressure induced in the sub-reservoirs so as to draw the blood from the sub-reservoirs and the blood-drawing line to the main reservoir. A controller has control sections each supplied with a negative pressure by a negative pressure source, and connected to the corresponding sub-reservoirs and the main reservoir by way of negative pressure lines so as to control the negative pressure in each of the sub-reservoirs and the main reservoir at a preset value.

6 Claims, 3 Drawing Sheets

PUMP-OXYGENATOR

BACKGROUND OF THE INVENTION

1. Field of the Invention

The present invention relates to a pump-oxygenator system which, during open heart surgery, has both cardiac pump function and pulmonary gas exchange function on the outside of a patient, and sucks and collects blood prevailing in the site being operated, etc., for recycling purposes

2. Prior Art

Leading functions of a pump-oxygenator are to store a pool of blood drawn from a patient in a reservoir, and use a roller pump to feed the blood stored in the reservoir into a heat exchanger or other suitable temperature regulation means where the blood is kept at a suitable temperature, and whence the blood is delivered to the patient upon subjected to gas exchange in artificial lungs.

Upon open heart surgery being performed, blood is emitted in the site being operated while some amounts of bloods stagnate in the pericardium, the heart, the main artery, etc. The blood emitted in the site being operated as well as the blood stagnating in the pericardium, the heart, the main artery, etc. are discarded at an initial stage of open heart surgery without being recycled.

In recent years, however, the blood emitted in the site being operated as well as the blood stagnating in the pericardium, the heart, the main artery, etc. have been capable of being collected in a reservoir for re-delivery to the patient using a roller pump, primarily because the roller pump used has improved performance.

However, much difficulty is involved in making a compact pump-oxygenator assembly including one or more sub-roller pumps in addition to the blood delivery roller pump. Thus, it is required to locate one or more such sub-roller pumps at positions spaced away from the patient; that is, the area occupied by the pump-oxygenator assembly in an operating room is unavoidably increased. This results in the following disadvantage:

a) The pump-oxygenator assembly has a possibility of interfering with operations by an operator who performs open heart surgery as well as assistants and, hence, obstructing smooth operations.

b) The overall length of tubes through which blood flows is increased, resulting in an increase in the amount of an electrolyte and other solution filled in the system, and so some considerable burdens being imposed on the patient.

c) With the area occupied by the pump-oxygenator assembly becoming large, it is awkward for an operator who manipulates the pump-oxygenator assembly to maintain careful yet overall inspection over it.

d) The pump-oxygenator assembly costs a lot.

Another conventional pump-oxygenator uses roller pumps for a blood delivery main pump and a suction sub-pump. The roller pump needs long preliminary periods prior to performing open heart surgery because of the need of conducting preliminary test-runs such as appropriate pressure closing tests for inspecting the engagement of rollers with tubes, and functionality tests. For this reason, it is unfeasible to perform quick operations in an emergency case.

Furthermore, the roller pump causes some damage to blood because the rollers have action on compressing blood in the tubes, and because it applies excessive loads on blood due to its mechanical driving.

Situations being like this, it is therefore an object of the present invention to provide a pump-oxygenator system which can not only be used with so great safety that burdens on a patient can be relieved but also readily manipulated with careful yet overall inspection maintained over it, and can be made compact at low cost.

SUMMARY OF THE INVENTION

According to the present invention, the aforesaid object is achieved by the provision of a pump-oxygenator system comprising:

(a) a main reservoir capable of storing a pool of blood supplied from a blood-drawing line and guiding the stored blood to a blood delivery line, (b) a pump located in said blood delivery line for supplying the blood stored in said main reservoir, (c) artificial lungs located in said blood delivery line for adding oxygen to a blood stream flowing through said blood delivery line and removing carbonic acid gas therefrom, (d) a plurality of sub-reservoirs located upstream of said main reservoir to store blood therein, (e) a plurality of sub-suction lines for blood, which are respectively connected to said plurality of sub-reservoirs, (f) a guidance means for guiding the bloods supplied into said plurality of sub-reservoirs to said main reservoir, and (g) a controller for independently subjecting interiors of said plurality of sub-reservoirs to negative pressure control.

Preferably, the plurality of sub-reservoirs are connected to the controller via a plurality of negative pressure lines.

Preferably, the controller is also capable of controlling a negative pressure in the main reservoir.

Preferably, the plurality of sub-reservoirs are bundled together, and provided separately from the main reservoir.

Preferably, the plurality of sub-reservoirs are bundled together upstream of the main reservoir, and the guidance means is dispensed with to feed the amounts of blood in the plurality of sub-reservoirs directly to the main reservoir.

Preferably, the pump is a centrifugal pump that drives a rotor to give centrifugal force to blood, so that the blood can be fed due to its own viscosity.

Preferably, each of the plurality of sub-reservoirs includes a built-in filter for removing blood coagulation.

The blood supplied from the blood-drawing line is stored in the main reservoir.

The controller is activated to generate negative pressures in the respective sub-reservoirs, whereby, without using sub-pumps as usual, blood (e.g., blood emitted in the site being operated, and blood stagnating in the pericardium, the heart, the main artery, etc.) can be fed directly into the sub-reservoirs. The blood supplied into each sub-reservoir is guided into the main reservoir via the guidance means.

A pool of blood stored in the main reservoir is guided to the blood delivery line including the pump as well as the artificial lungs. The pump delivers the blood to the patient while the thus delivered blood is subjected to gas exchange in the artificial lungs.

The pump-oxygenator system according to the present invention can be much simpler in construction and smaller in size than ever before, not only because of the use of a single pump but also because of the structure where blood emitted in the site being operated, and blood stagnating in the pericardium, the heart, the main artery, etc. are sucked directly into the respective sub-reservoirs without using sub-pumps as usual, and then guided to the main reservoir.

Thus, the pump-oxygenator made simple and small according to the present invention has the following advantages:

(i) Open heart surgery can be performed easily and smoothly, because the pump-oxygenator has little, if any, possibility of interfering with operations by both an operator and assistants.

(ii) The overall length of tubes through which blood flows can be so reduced that the amount of an electrolyte or other solution filled in the system can be reduced than ever before, thereby retrieving burdens on the patient.

(iii) The pump-oxygenator can be readily manipulated due to its size reduction, because the operator can maintain easy yet overall inspection thereover.

If the plurality of sub-reservoirs are connected to the controller via the plurality of negative pressure lines, the degree of freedom in the location of the controller can then be increased, so that the pump-oxygenator can be much more easily manipulated.

If the controller enables the negative pressure in the main reservoir to be regulated, it is then possible to regulate the amount of the blood to be drawn.

If the plurality of sub-reservoirs are bundled together and provided separately from the main reservoir, it is then possible to cut down the cost of the pump-oxygenator because an existing reservoir can be used as the main reservoir.

If the plurality of sub-reservoirs are bundled together upstream of the main reservoir with removal of the guidance means, it is then possible to make the pump-oxygenator much smaller because the space occupied by the sub-reservoirs and main reservoir can be reduced.

By use of a single centrifugal pump it is possible to achieve the following advantages:

The centrifugal pump dispenses with the preliminary test-runs needed for conventionally used roller pumps (e.g., appropriate pressure closing tests, and functionality tests); in other words, a preliminary time period prior to performing open heart surgery is shorter than usually required, so that quick operations can be performed in an emergency case.

The centrifugal pump causes lesser damage to blood than a roller pump does, so that burdens on the patient can be relieved.

The built-in filter for removal of blood coagulation, etc. in each of the plurality of sub-reservoirs ensures that the blood can be guided from the sub-reservoir into the main reservoir, and forecloses a possibility that the pump-oxygenator may be clogged up by the blood upon passed through the main reservoir.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The pump-oxygenator system according to the present invention will now be explained with reference to the accompanying drawings, which are given by of illustration only, and thus are not limitative of the present invention, and in which.

DETAILED EXPLANATION OF THE PREFERRED EMBODIMENTS

Figure 1:
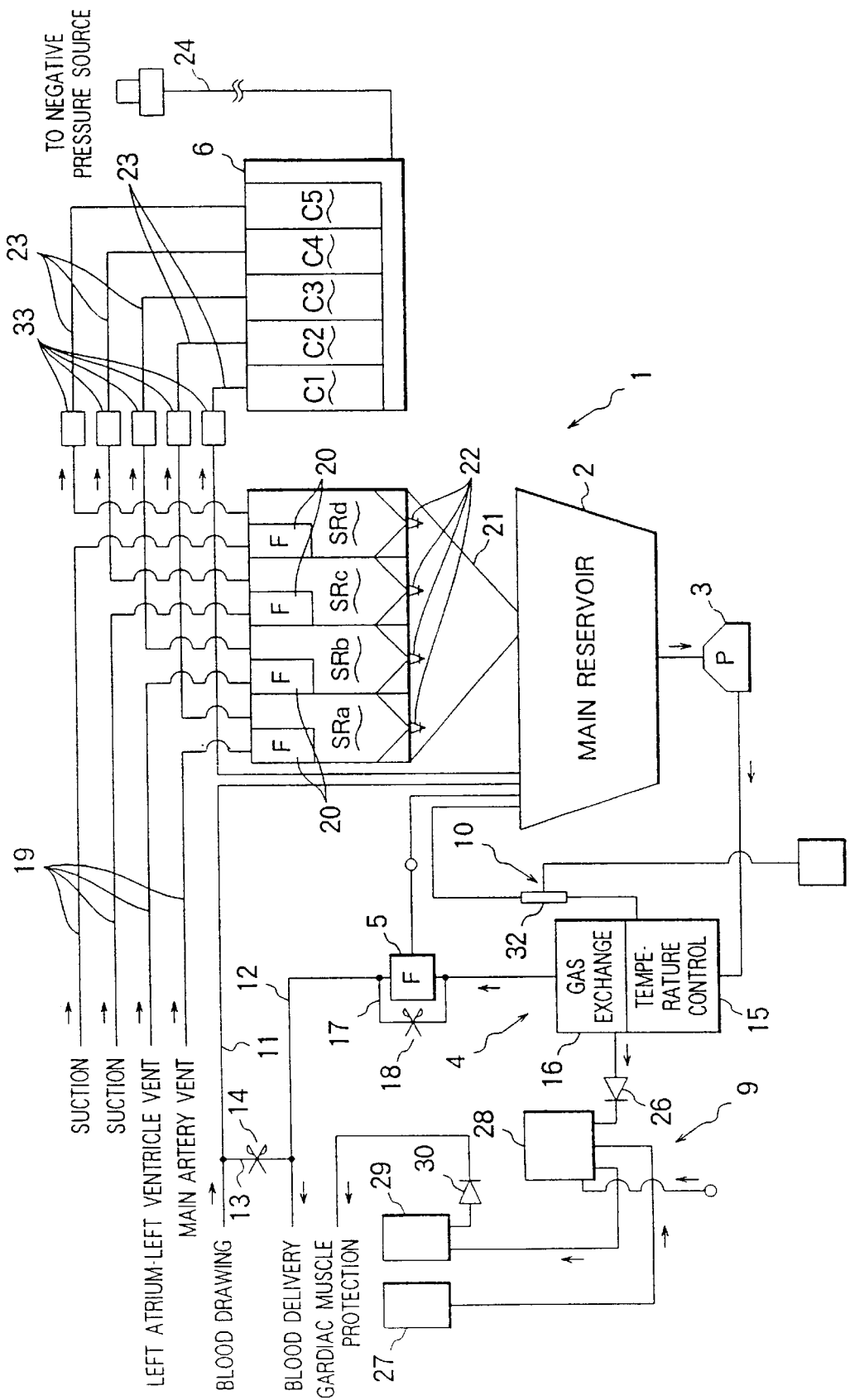
FIG. 1 is a block schematic of the pump-oxygenator system according to the present invention.

A pump-oxygenator system shown generally at 1 is built up of, as shown in FIG. 1, a main reservoir 2, a pump 3, artificial lungs 4, an arterial filter 5, four sub-reservoirs $SR_a$ to $SR_d$ (a main artery vent reservoir $SR_a$, a left atrium-left ventricle vent sub-reservoir $SR_b$, a first suction sub-reservoir $SR_c$, and a second suction sub-reservoir $SR_d$, as will be described later), and a controller 6 for independently controlling negative pressures within the main reservoir 2 as well as the four sub-reservoirs $SR_a$ to $SR_d$. The elements or parts forming the pump-oxygenator system 1 are built in a dedicated table (not shown) positioned in the vicinity of an operating bed (not shown).

Connected to the pump-oxygenator system I are a cardiac muscle protection circuit 9 for protecting the cardiac muscle and a filtering circuit 10 for subjecting a part of blood to ultrafiltration.

The main reservoir 2 is a closed vessel for provisionally storing patient's blood, and is connected at its upper portion with a blood-drawing line 11 that is connected to the venous side of the heart of the patient, so that blood on the venous side of the heart can be supplied into the main reservoir 2 by the siphon action of blood within the blood-drawing line 11 due to its own gravity and negative pressures in the main reservoir 2 (a suction negative pressure due to the activation of the pump 3, and a negative pressure controlled by the controller 6). Connected to a lower end of the main reservoir 2 is a blood delivery line 12 for feeding the blood stored therein back to the arterial side of the heart of the patient. This blood delivery line 12 includes the pump 3, artificial lungs 4 and arterial filter 5 as will described later.

As shown, a bypass tube 13 is provided to make connection between the blood-drawing line 11 and the blood delivery line 12, and bypass the respective elements of the pump-oxygenator system 1, and is closed up as by an extractor 14 when the pump-oxygenator system 1 is used (or when the use of the pump-oxygenator system 1 is initiated or finished).

The pump 3 is located in the blood delivery line 12 to suck the blood stored in the main reservoir 2 so that the blood can be delivered to the patient via the artificial lungs 4 and arterial filter 5. Preferably, a centrifugal pump is used as the pump 3. The centrifugal pump drives a rotor by means of a motor (not shown) to impart centrifugal force to blood, so that the blood can be fed out due to its own viscosity.

The artificial lungs 4 are located in the blood delivery line 12, and are composed of a temperature control section 15 for keeping the blood to be delivered to the patient at an appropriately controlled temperature and a gas exchange section 16 for adding oxygen to the blood to be delivered to the patient and removing carbonic acid gas therefrom.

In one specific embodiment of the temperature control section 15, heat exchange occurs between the blood flowing through the temperature control section 15 and externally supplied warm water, so that the blood can be controlled at a temperature fit for the patient.

In one specific embodiment of the gas exchange section 16, gas exchange takes place through a membrane. A compact hollow thread type of artificial pulmonary module is preferably used for this purpose.

The arterial filter 5 is located in the blood delivery line 12 through which the blood flows upon passed through the pump 3 and artificial lungs 4 for the purpose of removing coagulated blood, fine impurities, air bubbles, etc. from the blood to be fed back to the patient.

It is here to be understood that a filter bypass tube 17 located to bypass the arterial filter 5 is normally closed up as by an extractor 18.

Four sub-reservoirs $SR_a$ to $SR_d$ are each a closed vessel capable of storing an amount of blood therein, and are bundled together upstream of the main reservoir 2.

More specifically, provision is made of the main artery vent reservoir $SR_a$ for sucking an amount of blood remaining stagnant in the main artery, the left atrium-left ventricle vent sub-reservoir $SR_b$ for sucking an amount of blood remaining stagnant in the left atrium and ventricle, the first suction sub-reservoir $SR_c$ for sucking an amount of blood emitted out of the pericardium enclosing the heart, and the second suction sub-reservoir $SR_d$ for sucking an amount of blood emitted in the pericardium.

The aforesaid four sub-reservoirs $SR_a$ to $SR_d$ are respectively connected to sub-suction lines 19 for guiding the blood of the patient into them.

The respective sub-reservoirs $SR_a$ to $SR_d$ include therein sub-filters 20 for eliminating coagulated blood from the blood guided from the associated sub-suction lines 19 therein.

Connected to a lower portion of an assembly of four sub-reservoirs $SR_a$ to $SR_d$ is a funnel form of guidance means 21 for guiding the blood supplied into the sub-reservoirs $SR_a$ to $SR_d$ into the main reservoir 2 located underneath it. It is here to be noted that the sub-reservoirs $SR_a$ to $SR_d$ are provided with check valves 22 at their lower portions.

The four sub-reservoirs $SR_a$ to $SR_d$ are respectively connected to the controller 6 via four negative pressure lines 23, in which negative pressure line filters 33 are provided for the purpose of protecting the controller 6.

The controller 6 independently maintains the interiors of the four sub-reservoirs $SR_a$ to $SR_d$ at negative pressures, and controls such negative pressures. In the instant embodiment, it is to be noted that the negative pressure in the main reservoir 2, too, is controllable by this controller through the negative pressure lines 23.

The controller 6 includes a tube form of connector 24 that is connected to a negative pressure source located on a wall surface or the like of an operating room. The negative pressures in the sub-reservoirs may be regulated within one exemplary range of 0 to 50 mmHg by the negative pressure obtained through this connecting tube 24.

The controller 6 comprises a main control section C1 for controlling the negative pressure in the main reservoir 2, a main artery vent control section C2 for controlling the negative pressure in the main artery vent sub-reservoir $SR_a$, a left atrium-left ventricle vent control section C3 for controlling the negative pressure in the left atrium-left ventricle vent sub-reservoir $SR_b$, a first suction control section C4 for controlling the negative pressure in the first suction sub-reservoir $SR_c$, and a second suction control section C5 for controlling the negative pressure in the second suction sub-reservoir $SR_d$.

Figure 2:
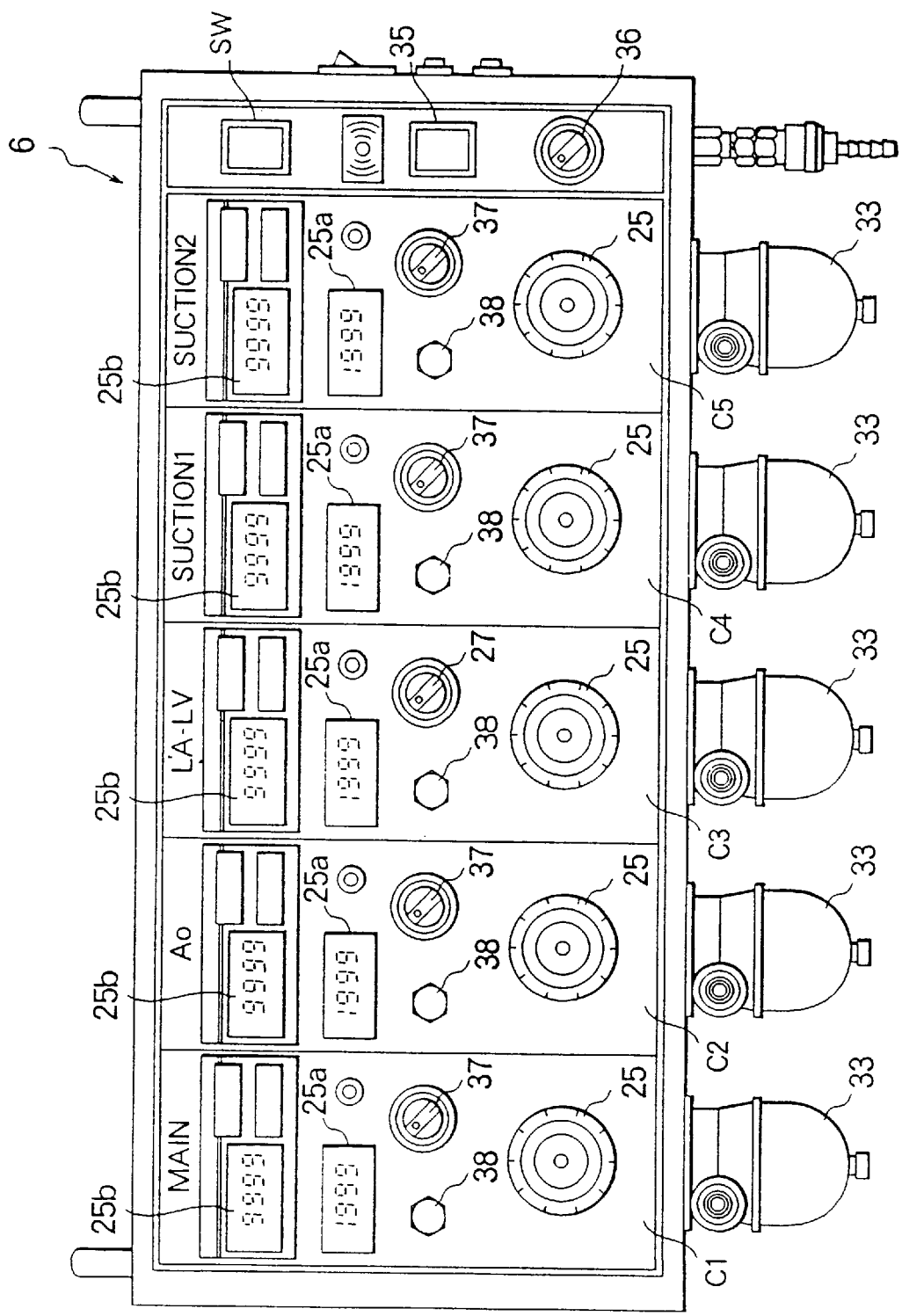
FIG. 2 is a front view of the controller according to the present invention.

As shown in FIG. 2, it is to be noted that each of the control sections C1 to C5 includes a regulating knob 25 for the manual presetting of negative pressure as well as a display 25*a* for displaying the amount of blood drawn and a negative pressure display screen 25*b*.

Figure 3:
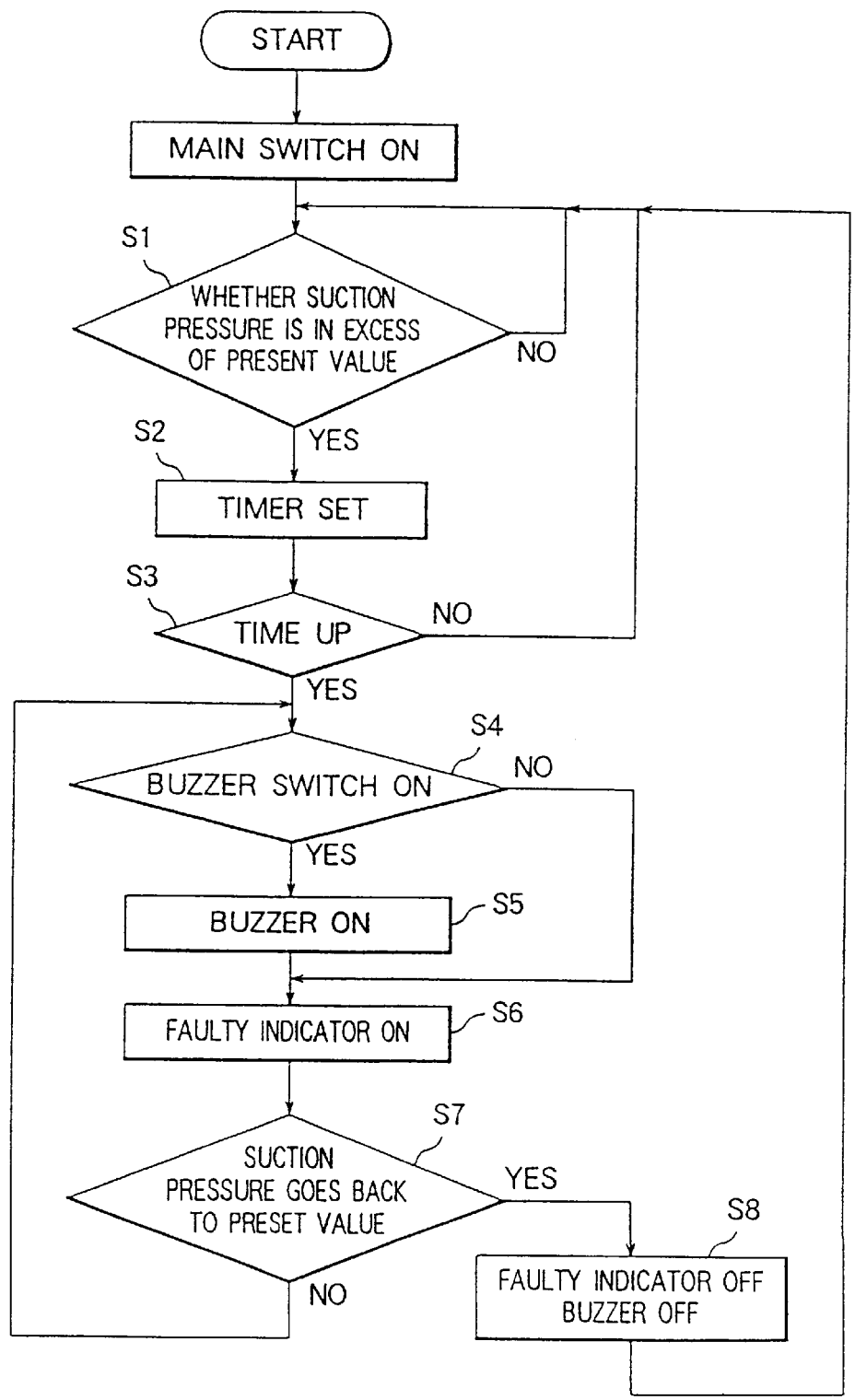
FIG. 3 is a flowchart of the fault sensor means according to the present invention.

The controller 6 includes a fault sensor means for sensing faulty negative pressure, if any, for each of the control sections C1 to C5. This faulty negative pressure sensor means (for sensing faulty suction pressure) will now be explained with reference to the flowchart attached hereto as FIG. 3.

Upon a main switch SW turned on (start), judgment is passed on whether or not the negative pressure detected exceeds a preset value (Step S1). If the answer is "NO", the controller goes back to Step 1. If the answer is "YES", a timer for counting a given length of time is started (Step S2), and judgment is then passed on whether or not the timer is timed up (Step S3). If the answer is "NO", the controller goes back to step S1.

If the answer is "YES" at Step 33, judgment is passed on whether or not a buzzer switch (not shown) is turned on (Step S4). If the answer is "YES", a buzzer (not shown) is turned on (Step S5) to light a faulty indicator (not shown) on (Step S6). If the answer is "NO". at Step S4, the controller goes to Step S6 to light the faulty indicator on.

Upon Step S6 executed, judgment is passed on whether or not the negative pressure detected has returned back to the preset range (Step S7). If the answer is "NO", the controller goes back to Step S4. If the answer is "YES", the faulty indicator as well as the buzzer is turned off (Step S8). Thereafter, the controller goes back to Step S1.

While a single buzzer and a single faulty indicator are used with the controller, it is to be understood that a faulty indicator may be used independently for each of the control sections C1 to C5. It is also to be noted that instead of the buzzer, an alarm or chime may be used for the purpose of giving sound or other acoustic warning.

Such a faulty sensor means as shown in the flowchart and provided for each of the control sections C1 to C5 ensures that an operator can use the controller 6 to detect faulty negative pressure, so that the reliability of the pump-oxygenator system 1 can be increased.

In FIG. 2 showing the controller 6, it is to be noted that reference numeral 35 represents a buzzer changeover switch, 36 a negative pressure main switch, 37 a negative pressure selection switch provided independently for each of the control sections C1 and C5, and 38 a flow rate regulation valve designed to regulate the flow rate of the blood sucked.

The cardiac muscle protection circuit 9 and filtration circuit 10 incorporated in the pump-oxygenator system 1 according to the instant embodiment will now be explained.

The cardiac muscle protection circuit 9 is a circuit for feeding therefrom a mixture of a part of the blood pumped out by the pump 3 with a cardiac muscle protection agent. In the instant embodiment, this circuit includes a chamber 28 for squeezing out the blood drawn out of the artificial lungs 4 through the check valve 26 and a cardiac muscle protection agent (GIK) 27. The thus squeezed-out mixture-is then delivered to the heart of the patient via a combined pressure and temperature meter 29 and a check valve 30.

The filtration circuit 10 is a circuit for returning a part of the blood pumped out by the pump 3 back to the main reservoir 2 after ultrafiltration. In the instant embodiment, the blood drawn out of the artificial lungs 4 is subjected to ultratiltration through an ultrafilter 32, and then fed back to the main reservoir 2.

The pump-oxygenator system 1 of the present invention works as follows.

The function of the pump-oxygenator 1 is activated by putting the functioning elements inclusive of the pump 3, controller 6, and a warm water circuit of temperature regulator 15 in operation, and closing the bypass tube 13 making connection between the blood-drawing line 11 and the blood delivery line 12 using the extractor 14 or the like.

The drawn blood is guided into the main reservoir 2 from the blood-drawing line 11 connected to the venous side of the heart of the patient by the siphon action of blood due to its own gravity as well as by the negative pressure introduced in the main reservoir 2 due to the suction negative pressure of the pump 3 and the suction negative pressure by the main control section C1, and that blood is then stored in the main reservoir 2.

On the other hand, the main artery vent control section C2, left atrium-left ventricle vent control section C3, first suction control section C4 and second suction control section C5 of the controller 6 are maintained at the predetermined negative pressures, so that the interiors of the main artery vent sub-reservoir $SR_a$, left atrium-left ventricle vent sub-reservoir $SR_b$, first suction sub-reservoir $SR_c$ and second suction sub-reservoir $SR_d$ are kept at the predetermined negative pressures.

Thereupon, blood stagnating in the main artery, blood remaining stagnant in the left atrium and ventricle, blood emitted out of the pericardium enclosing the heart, and blood emitted in the pericardium are sucked through their associated suction lines into the main artery vent,sub-reservoir $SR_a$, left atrium-left ventricle vent sub-reservoir $SR_b$, first suction sub-reservoir $SR_c$ and second suction sub-reservoir $SR_d$.

The blood guided into the main artery vent sub-reservoir $SR_a$, left atrium-left ventricle vent sub-reservoir $SR_b$, first suction sub-reservoir $SR_c$ and second suction sub-reservoir $SR_d$ is then passed through their associated sub-filters 20 to remove blood coagulation, and stored therein. Then, this blood is guided into the main reservoir 2 through the guidance means 21.

A pool of blood stored in the main reservoir 2 is guided to the blood delivery line 12, and is then delivered to the venous side of the patient by the pump 3 located in the blood delivery line 12. Subsequently, the blood is passed through the temperature regulation section 15 of the pump-oxygenator where its temperature is suitably regulated, and then through the gas exchange section 16 where the blood to be delivered to the patient is provided with oxygen and deprived of carbonic acid gas.

While the pump-oxygenator system 1 is working, the aforesaid operations take place continuously.

The pump-oxygenator according to the present invention can be much simpler in construction and smaller in size than ever before, not only because of the use of a single pump 3 but also because of the structure where blood emitted in the site being operated, and blood remaining stagnant in the pericardium, the heart, the main artery, etc. are sucked directly into the respective sub-reservoirs $SR_a$ to $SR_d$ without using sub-pumps as usual, and then guided to the main reservoir 2.

Thus, the pump-oxygenator 1 made simple and small according to the present invention has the following advantages:

Open heart surgery can be performed easily and smoothly, because the pump-oxygenator has little, if any, possibility of hindering operations by both an operator and assistants.

The overall length of tubes (blood-drawing line 11, sub-suction lines 19, blood delivery line 12, etc.) through which blood flows can be so reduced that the amount of an electrolyte or other solution filled in the system can be reduced than ever before, thereby retrieving burdens on the patient.

The pump-oxygenator 1 can be readily manipulated due to its size reduction, because the operator can maintain easy yet overall inspection thereover. Manipulation of the pump-oxygenator 1 (including pump 3, controller 6, temperature regulation section 15, etc.), and inspection of how tubes are connected to each other is easily achievable.

Since a negative pressure source provided on a wall surface or other part of an operating room can be used as the negative pressure source for sucking blood emitted in the site being operated as well as blood that stagnate in the pericardium, the heart, the main artery, etc., there is no need of using sub-pumps for sucking that blood or providing a separate negative pressure generator. This makes it possible to reduce the size and cost of the pump-oxygenator 1.

In the instant embodiment, the sub-reservoirs $SR_a$ to $SR_d$ are connected to the controller 6 via the plurality of negative pressure lines 23; the degree of freedom in the location of the controller 6 can be increased, so that the pump-oxygenator 1 can be much more easily manipulated under observation.

In the instant embodiment, by regulating the negative pressure in the main reservoir 2 by means of the controller 6, it is also possible to regulate the amount of the blood to be drawn.

In the instant embodiment, the sub-reservoirs $SR_a$ to $SR_d$ are bundled together and provided separately from the main reservoir 2, and so an existing reservoir can be used as the main reservoir 2.

By using a single centrifugal pump as the pump 3 it is possible to achieve the following advantages:

The centrifugal pump dispenses with the preliminary test-runs needed for conventionally used roller pumps (e.g., appropriate pressure closing tests); in other words, a preliminary time period prior to performing open heart surgery is shorter than usually required, so that quick operations can be performed in an emergency case.

The centrifugal pump used as the pump 3 causes lesser damage to blood than a roller pump does, so that burdens on the patient can be relieved.

The filter 20 for removal of blood coagulation built in each of the sub-reservoirs $SR_a$ to $SR_d$ ensures that the blood can be guided into the main reservoir 2 therefrom, and forecloses a possibility that the pump 3, artificial lungs 4, tubes, etc. may be clogged up by the blood upon passed through the main reservoir 2.

While the negative pressure in the main reservoir 2 is also controlled by the controller 6 in the instant embodiment, it is to be understood that it is not always required to control the negative pressure in the main reservoir 2 by means of the controller 6.

While the sub-reservoirs $SR_a$ to $SR_d$ are provided separately from the main reservoir 2 in the instant embodiment, it is to be understood that if the sub-reservoirs $SR_a$ to $SR_d$ are bundled together upstream of the main reservoir 2 with removal of the guidance means 21, it is then possible to guide the blood in the sub-reservoirs $SR_a$ to $SR_d$ directly into the main reservoir 2, thereby making the pump-oxygenator 1 much smaller because the area occupied by the sub-reservoirs $SR_a$ to $SR_d$ and main reservoir 2 can be reduced.

While a negative pressure source mounted on a wall surface or other part of an operating room is used as the negative pressure in the instant embodiment, it is to be understood that use may be made of a negative pressure source designed for pump-oxygenators.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pump-oxygenator comprising:

(a) a main reservoir capable of storing an amount of blood supplied from a blood-drawing line and guiding the stored blood to a blood delivery line, (b) a pump located in said blood delivery line for supplying the blood stored in said main reservoir, (c) artificial lungs located in said blood delivery line for adding oxygen to a blood stream flowing through said blood delivery line and removing carbonic acid gas therefrom, (d) a plurality of sub-reservoirs located upstream of said main reservoir to store blood therein, (e) a plurality of sub-suction lines for blood, which are respectively connected to said plurality of sub-reservoirs, (f) guidance means for guiding the blood supplied to said plurality of sub-reservoirs to said main reservoir, (g) said pump being driven to supply a negative pressure with said main reservoir, a magnitude of the negative pressure being smaller than a negative pressure induced in said sub-reservoirs so as to draw the blood from said sub-reservoirs and said blood-drawing line to said main reservoir, and (h) a controller having control sections each supplied with a negative pressure by a negative pressure source, and connected to corresponding sub-reservoirs and the main reservoir by way of negative pressure lines so as to control the negative pressure in each of said sub-reservoirs and said main reservoir individually at a preset value.

2. The pump-oxygenator as recited in claim 1, wherein said plurality of sub-reservoirs are bundled together, and provided separately from said main reservoir.

3. The pump-oxygenator as recited in claim 1, wherein said plurality of sub-reservoirs are bundled together upstream of said main reservoir, and said guidance means is dispensed with to feed the bloods in said plurality of sub-reservoirs directly to said main reservoir.

4. The pump-oxygenator as recited in claim 1, wherein said pump is a centrifugal pump that drives a rotor to give centrifugal force to blood, so that the blood can be fed due to its own viscosity.

5. The pump-oxygenator as recited in claim 1, wherein said plurality of sub-reservoirs each includes a built-in filter for removing blood coagulation.

6. The pump-oxygenator as recited in claim 1, wherein the controller includes fault sensor means for sensing faulty negative pressure by judging whether or not the negative pressure exceeds a preset value.

* * * * *